United States Patent
Fujita

(10) Patent No.: US 8,114,012 B2
(45) Date of Patent: Feb. 14, 2012

(54) CAPSULE ENDOSCOPE AND INTRASUBJECT MEDICAL SYSTEM USING SAME

(75) Inventor: Manabu Fujita, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1197 days.

(21) Appl. No.: 11/825,248

(22) Filed: Jul. 5, 2007

(65) Prior Publication Data

US 2008/0071139 A1 Mar. 20, 2008

(30) Foreign Application Priority Data

Jul. 5, 2006 (JP) .................................. 2006-185527

(51) Int. Cl.
*A61B 1/00* (2006.01)

(52) U.S. Cl. ....................................... 600/114; 600/102

(58) Field of Classification Search .................. 600/101, 600/103, 104, 106, 117, 118, 132, 136, 146, 600/149, 102, 114; 606/113; 604/103.03
See application file for complete search history.

(56) References Cited

U.S. PATENT DOCUMENTS

| 5,984,860 A * | 11/1999 | Shan | 600/116 |
| 2004/0111020 A1 * | 6/2004 | Long | 600/407 |

FOREIGN PATENT DOCUMENTS

| JP | 2000-33070 | 2/2000 |
| JP | 2004-181250 | 7/2004 |
| JP | 2000-229922 | 8/2004 |

* cited by examiner

*Primary Examiner* — John P Leubecker
*Assistant Examiner* — Christopher Sponheimer
(74) *Attorney, Agent, or Firm* — Scully, Scott, Murphy & Presser, P.C.

(57) ABSTRACT

A capsule endoscope includes a string that has one end attached to a main body of the capsule endoscope and another end secured at a predetermined position, and a wind-up unit that is provided in the main body of the capsule endoscope to bring out and wind up the string.

11 Claims, 6 Drawing Sheets

CAPSULE ENDOSCOPE AND INTRASUBJECT MEDICAL SYSTEM USING SAME

CROSS-REFERENCE TO RELATED APPLICATIONS

This application is based upon and claims the benefit of priority from Japanese Patent Application No. 2006-185527, filed Jul. 5, 2006, the entire contents of which are incorporated herein by reference.

BACKGROUND OF THE INVENTION

1. Field of the Invention

The present invention relates to a capsule endoscope performing various medical treatments including examinations and treatments in a body cavity in a subject, and to an intrasubject medical system using the same; in particular, the present invention relates to a capsule endoscope having a string whose one end is attached to a main body of the capsule endoscope and whose another end is arranged outside a subject, and to an intrasubject medical system using the same.

2. Description of the Related Art

In recent years, swallowable capsule endoscopes appear in the field of endoscope. The capsule endoscope has an imaging function and a radio communication function. The capsule endoscope has a function of traveling through inside a body cavity, such as an interior of an internal organ such as stomach and small intestine, following peristaltic movements thereof and sequentially capturing images after being swallowed by a patient from the mouth for an observation (examination) until naturally excreted from a human body.

While traveling inside the body cavity, image data captured inside the body by the capsule endoscope is sequentially transmitted to an outside by radio communication, and is stored in a memory provided in an external receiver. When the patient carries the receiver which has a radio communication function and a memory function, the patient can move freely even during a period after swallowing the capsule endoscope until excreting the same. Thereafter, a doctor or a nurse can make diagnosis by displaying an image of an organ on a monitor based on the image data accumulated in the memory.

Here, since the capsule endoscope described above is small and easily swallowable, images inside the subject can be easily obtained without the need of anesthesia in comparison with an ordinary endoscope. It is possible to attach one end of a string to a main body of the capsule endoscope and arrange another end outside the body, and manipulate the string from outside the body to control a position of the capsule endoscope so as to obtain a desirable image (see, for example, Japanese Patent Application Laid-Open No. 2004-181250 and Japanese Patent Application Laid-Open No. 2000-33070).

On the other hand, there is a capsule endoscope in which a magnet is embedded in a main body thereof; a rotating magnetic field is applied externally to rotate the magnet, and in turn, to rotate the capsule endoscope, whereby the capsule endoscope is made to freely move inside the subject (see, for example, Japanese Patent Application Laid-Open No. 2004-229922).

However, when the conventional capsule endoscope to which a string is attached as described above is used, a problem arises; namely, the attached string successively rubs against a pharyngeal region thereby hurting the pharyngeal region.

Further, when the conventional capsule endoscope which is rotated by the external rotating magnetic field is made to move inside an organ such as stomach that has a wide space, the capsule endoscope sometimes becomes unable to move off from a specific wall, and this raises a problem that a desirable image cannot be obtained.

SUMMARY OF THE INVENTION

It is an object of the present invention to at least solve the problems as described above.

A capsule endoscope according to one aspect of the present invention includes a string that has one end attached to a main body of the capsule endoscope and another end secured at a predetermined position, and a wind-up unit that is provided in the main body of the capsule endoscope to bring out and wind up the string.

An intrasubject medical system according to another aspect of the present invention includes a capsule endoscope having a string whose one end is attached to a main body of the capsule endoscope and whose another end is secured at a predetermined position, the capsule endoscope including inside the main body of the capsule endoscope an imaging unit, a radio transmitting unit that radio transmits an image captured by the imaging unit to an outside of a subject, a wind-up unit that brings out and winds up the string, and a magnet that is connected to the wind-up unit and rotates according to an external rotating magnetic field, the capsule endoscope brings out and winds up the string in conjunction with rotation of the magnet, a receiving device that receives an image transmitted from the capsule endoscope, and an external rotating magnetic field generating device that generates the external rotating magnetic field to rotate the magnet.

An intrasubject medical system according to still another aspect of the present invention includes a capsule endoscope having a string whose one end is attached to a main body of the capsule endoscope and whose another end is secured at a predetermined position, the capsule endoscope including inside the main body of the capsule endoscope an imaging unit, a radio transmitting unit that radio transmits an image captured by the imaging unit to an outside of a subject, a wind-up unit that brings out and winds up the string, and a driving unit that is connected to the wind-up unit and rotates the wind-up unit to bring out and wind up the string, and a control unit that controls driving of the driving unit by receiving an external control signal including a magnetic field, a receiving device that receives the image transmitted from the capsule endoscope, and an external control signal generating device that transmits the external control signal to the control unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule endoscope and an intrasubject medical system using the same according to the present invention will be described below with reference to the drawings. The present invention is not limited by the embodiments.

First Embodiment

Figure 1:
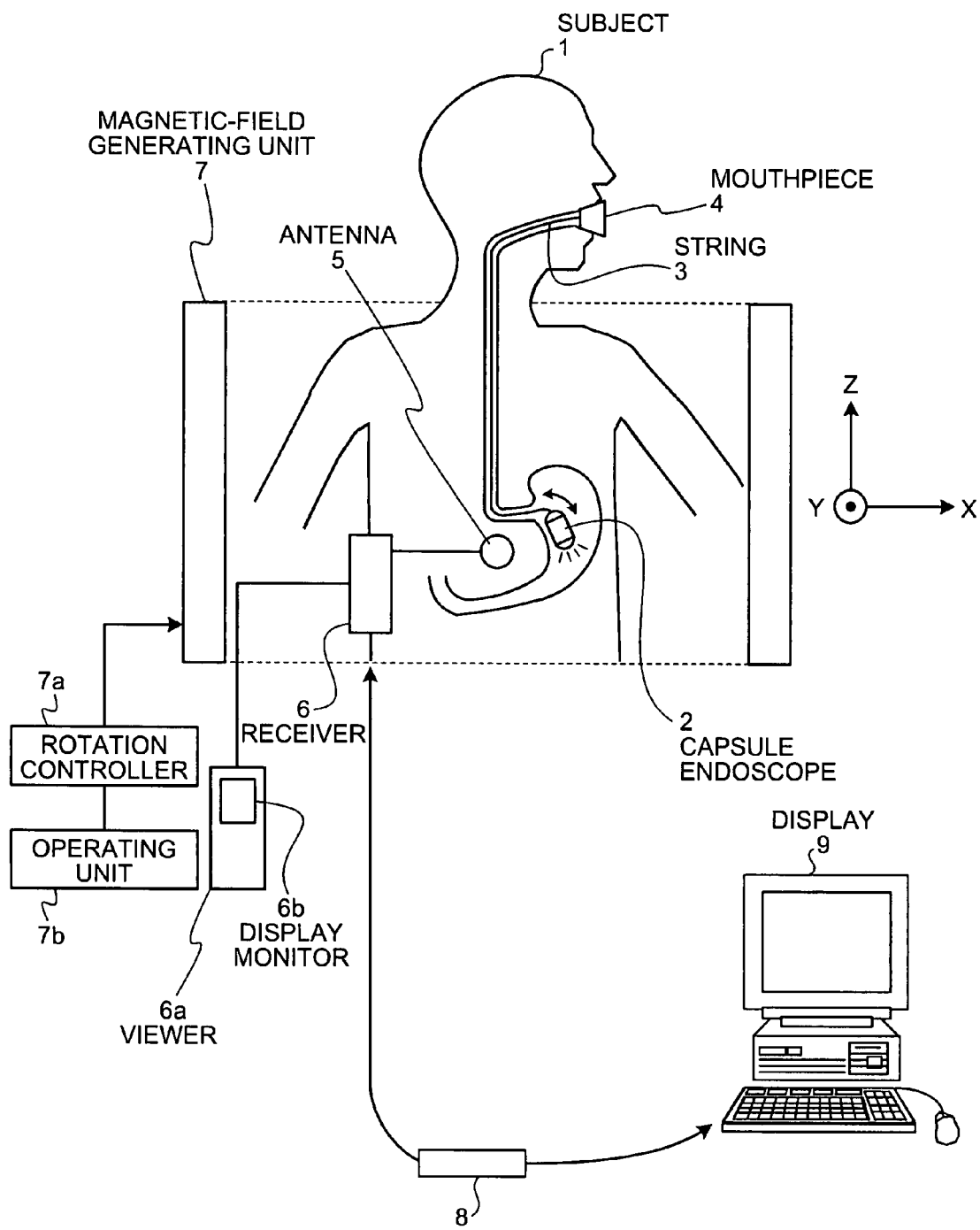
FIG. 1 is a diagram showing an overall configuration of an intrasubject medical system according to a first embodiment of the present invention.
Figure 2:
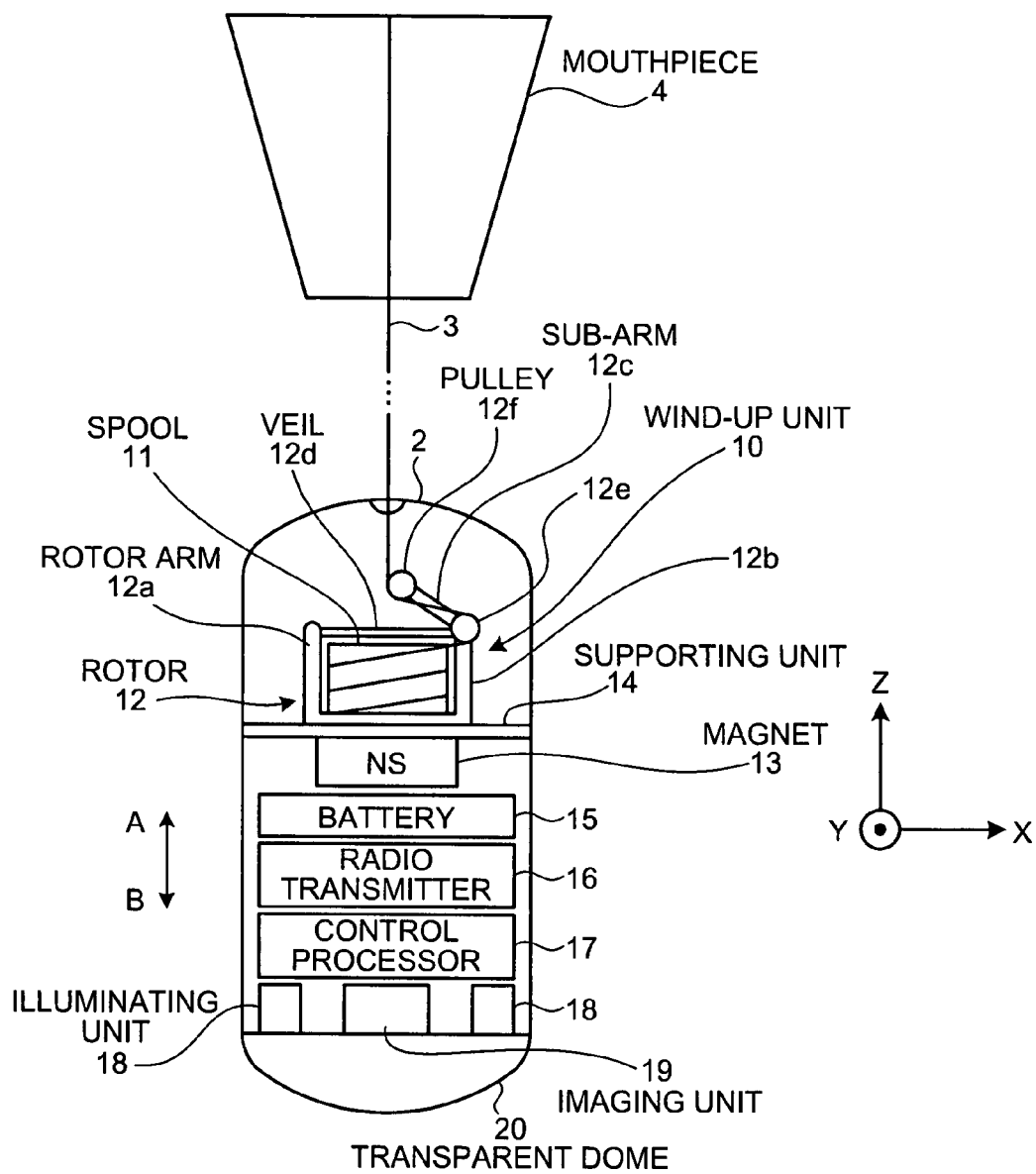
FIG. 2 is a sectional view showing a configuration of a capsule endoscope shown in FIG. 1.

FIG. 1 is a diagram showing an overall configuration of an intrasubject medical system according to a first embodiment of the present invention. Further, FIG. 2 is a sectional view showing a configuration of a capsule endoscope used in the intrasubject medical system shown in FIG. 1. In FIG. 1, the intrasubject medical system includes a capsule endoscope 2 which is inserted into an interior of a subject 1. To the capsule endoscope 2, one end of a string 3 is attached, and another end of the string 3 is secured to a mouthpiece 4. As shown in FIG. 1, when the capsule endoscope 2 is inserted into the interior of the subject 1, since the another end of the string 3 is secured by the mouthpiece 4, a position of the capsule endoscope 2 is determined by a length of the string 3. Here, the capsule endoscope 2 has, as described later, a wind-up unit which brings out and winds up the string 3, and a relative positional relation between the mouthpiece 4 and the capsule endoscope 2 is determined by bringing-out and winding-up, whereby the capsule endoscope 2 itself can move without the need of movement of the string 3.

On a surrounding surface of the subject 1, a receiver 6 is arranged, and one or more antenna 5 is arranged on a surface site of the subject 1 near the position where the capsule endoscope 2 is positioned from the receiver 6. The receiver 6 receives an image of the interior of the subject 1 via the antenna 5 as transmitted from the capsule endoscope 2.

A display 9 serves to display an image captured by the capsule endoscope 2, for example, and is implemented with a workstation, for example, that performs image display based on data obtained by a portable recording medium 8. The portable recording medium 8 is attachable/detachable to/from the receiver 6 and the display 9, and when attached to these devices, information can be output and recorded. In the first embodiment, while images are captured inside the subject 1, the portable recording medium 8 is attached to the receiver 6 so as to record information such as received images, and when the image-capture inside the subject 1 is finished, the portable recording medium 8 is attached to the display 9 so that the display 9 reads out the information such as images recorded in the portable recording medium 8. The portable recording medium 8 may not be used, and the receiver 8 and the display 9 may be directly connected by a cable or by radio.

Further, a viewer 6a is attachable/detachable to/from the receiver 6, and displays information such as images received by the receiver 6 in real time on a display monitor 6b. When the portable recording medium 8 is not used and the receiver 6 and the display 9 are directly connected by a cable or by radio, the display 9 can display the captured images and the like in real time, and therefore, the viewer 6a may not be used.

Figure 3:
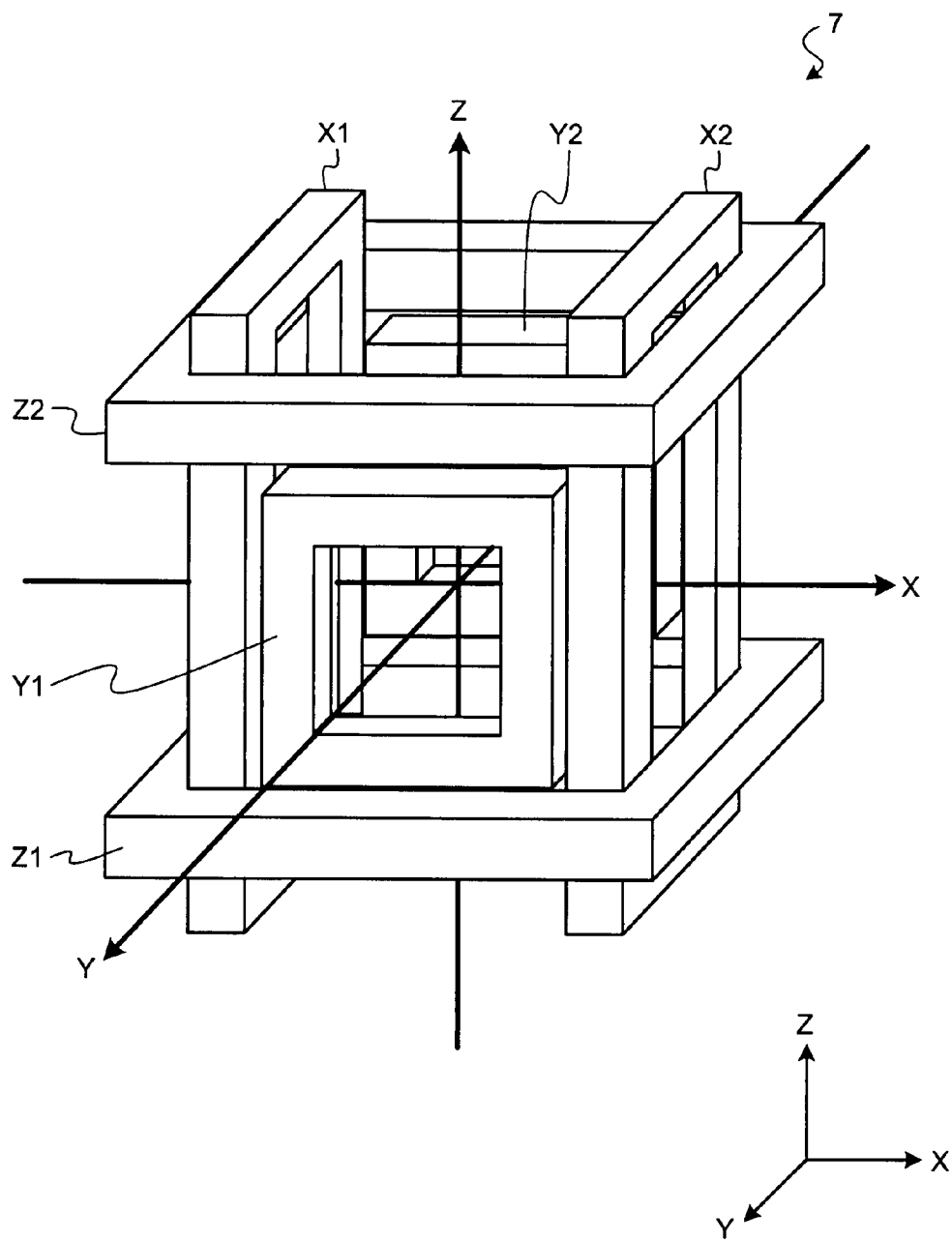
FIG. 3 is a perspective view showing a configuration of a magnetic-field generating unit shown in FIG. 1.

A magnetic-field generating unit 7 is an electromagnet which is formed with a high dielectric constant member such as ferromagnetic body around which a coil is wound, and is configured as combined pairs of electromagnets arranged so as to sandwich the subject 1 in three directions, i.e., in X, Y, and Z directions as shown in FIG. 3 (more specifically, a pair of electromagnets X1 and X2 in X-direction, a pair of electromagnets Y1 and Y2 in Y-direction, and a pair of electromagnets Z1 and Z2 in Z-direction), and when the strength of the magnetic field generated in each direction is controlled, a three-dimensional external rotating magnetic field can be generated for the subject 1. The formation of the external rotating magnetic field is realized by a rotation controller 7a which controls an amount of conducting power to the electromagnets in each direction of the magnetic-field generating unit 7 according to an operation instruction from an operating unit 7b. A magnet is arranged in the capsule endoscope 2, and when the magnet rotates under the influence of the external rotating magnetic field, the wind-up unit mentioned earlier brings out or winds up the string 3. An operator manipulates the operating unit 7b while monitoring an image captured by the capsule endoscope 2 and displayed on the display monitor 6b of the viewer 6a or on a display monitor of the display 9.

The capsule endoscope 2 will be described with reference to FIG. 2. The capsule endoscope 2 is a cylindrical member whose two ends are formed in spherical surfaces, and is covered by a "capsule-type" package member. In the package member, a wind-up unit 10 that brings out and winds up the string 3, a magnet 13 that rotates according to the external rotating magnetic field to cause the wind-up unit 10 to bring out or wind up the string, a battery 15, a radio transmitter 16, a control processor 17, an illuminating unit 18, and an imaging unit 19 are provided, and the battery 15, the radio transmitter 16, the control processor 17, the illuminating unit 18, and the imaging unit 19 are connected by a flexible wiring and arranged in an alternately folded manner.

The string 3 is attached to a spherical surface side at one end of the cylindrical member, and another end of the cylindrical member is covered with a semispherical transparent dome 20. At the side of the transparent dome 20, the imaging unit 19 is arranged substantially at a center of a central axis of the cylindrical member, and the illuminating unit 18 implemented with an LED or the like is arranged around the imaging unit 19. The imaging unit 19 acquires an image of a site illuminated by light emitted from the illuminating unit 18 using an imager such as a CCD and transmits the acquired image to the control processor 17. The acquired image is processed as image data by the control processor 17, and is transmitted from the radio transmitter 16 through an antenna not shown in the radio transmitter 16 to an outside of the subject 1. The control processor 17 usually acquires two frames of image data every one second and transmits the acquired image to the outside of the subject 1, however, the imaging interval may be shorter or longer.

The wind-up unit 10 and the magnet 13 are supported by a supporting unit 14 which is a disk secured to the cylindrical member and vertically extends relative to the central axis of the cylindrical member, and the magnet 13 is arranged at the supporting unit 14 at the side of the transparent dome 20, whereas the wind-up unit 10 is arranged at an opposite side. The wind-up unit 10 is configured like a spinning reel, and includes a columnar spool 11 that is secured on the supporting unit 14 to wind up the string and a rotor 12 that rotates around the spool 11, and the rotation of the rotor 12 is linked to the rotation of the magnet 13.

The rotor 12 has a pair of rotor arms 12a and 12b that rotates around an outer circumference of the spool 11, and an end of each of the rotor arms 12a and 12b is supported by a semicircular veil 12d at an outer circumference of the spool 11. A sub-arm 12c is arranged at an end of the rotor arm 12b inclined towards the side of the central axis, and pulleys 12e and 12f are arranged at a portion connecting the rotor arm 12b and the sub-arm 12c and at an end of the sub-arm 12c, respectively, to guide the string 3.

The string 3 secured to the mouthpiece 4 is inserted into the capsule endoscope 2 from a center of a dome portion opposite to the transparent dome 20, and is guided by the pulleys 12f and 12e to be wound around a columnar side surface of the spool 11.

When an external rotating magnetic field is applied around the central axis of the capsule endoscope 2 from the magnetic-field generating unit 7, the magnet 13 rotates, and the rotor 12 rotates, for example, around the central axis of the capsule endoscope 2 in conjunction with the magnet 13. Meanwhile, since the spool 11 is secured, when the magnet 13 rotates in a winding direction A, the string 3 is wound up by the spool 11, and the capsule endoscope 2 moves to the side of the mouthpiece 4. On the other hand, when the magnet 13 rotates in a feeding direction B, the string 3 is brought out from the spool 11, and the capsule endoscope 2 moves in such a direction as to move away from the side of the mouthpiece 4. In brief, the rotation of the magnet 13 caused by the external rotating magnetic field can make the string 3 wound up on or brought out from the wind-up unit 10 so as to move the capsule endoscope 2 in the subject without causing the movements of the string 3.

In the first embodiment, as described above, when the capsule endoscope 2 is made to move, the string 3 does not move, and the movements are caused by the winding-up or bringing-out of the string 3 by the capsule endoscope 2 itself, whereby the pharyngeal region is not hurt and desirable images can be obtained from throughout an interior of an organ even when the organ has a wide space as in the stomach.

Though the spool 11 is fixed so as not to rotate, the spool 11 may include an oscillating mechanism which causes vertical movements along the central axis direction according to the rotation of the magnet 13 so that the wound-state of the string 3 is made flat.

Figure 4:
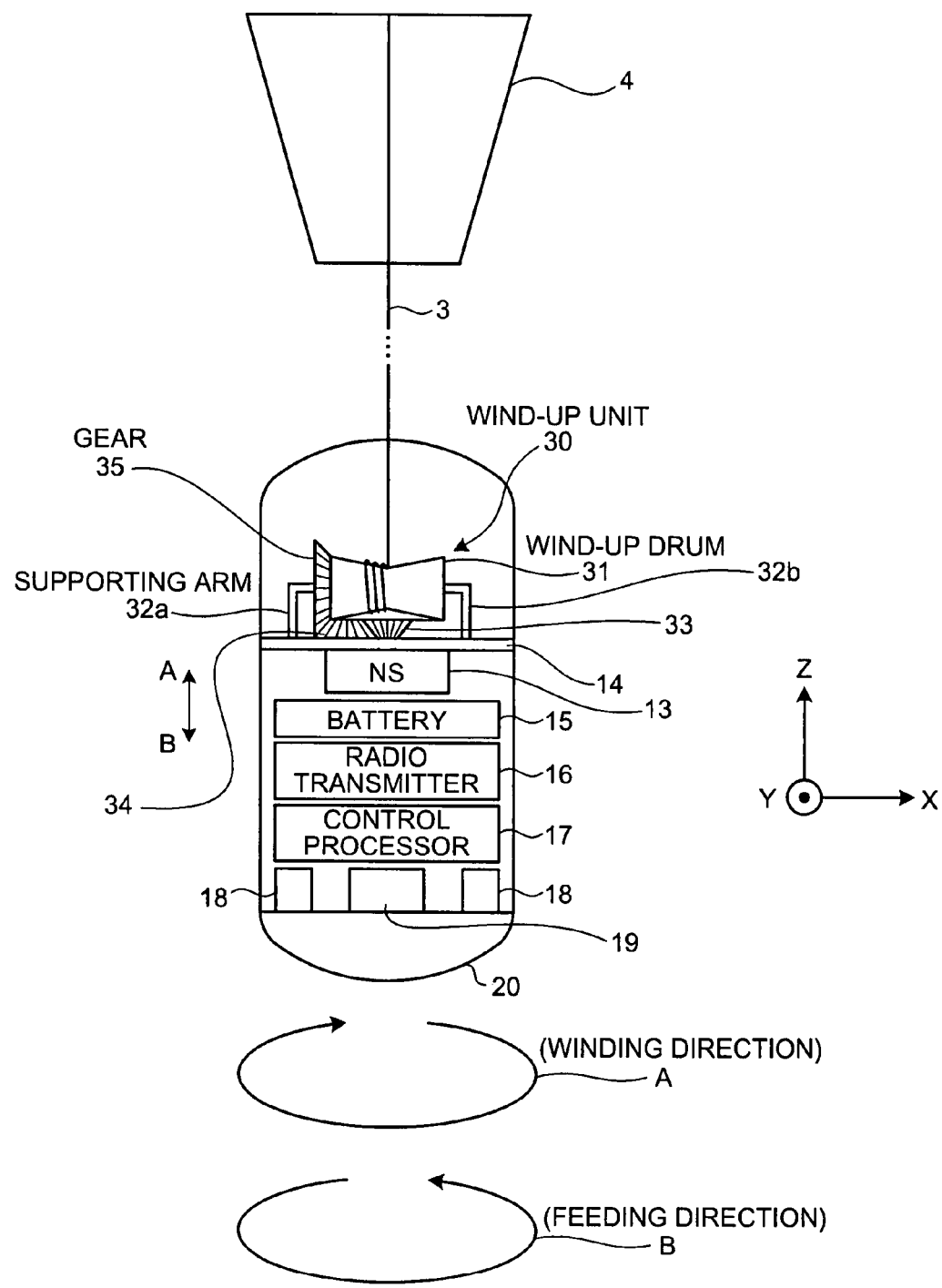
FIG. 4 is a sectional view showing a configuration of a capsule endoscope according to a modification of the first embodiment of the present invention.

In the first embodiment described above, the spool 11 is secured and made to wind up the string 3 in the direction of rotation of the magnet 13, however, not limited thereto, the string 3 may be wound up around an axis orthogonal to the axis of rotation of the magnet 13 as shown in FIG. 4. In a capsule endoscope 2a according to a modification of the first embodiment shown in FIG. 4, a wind-up drum 31 is provided in place of the spool 11, and the wind-up drum 31 is made to rotate about the axis orthogonal to the axis of rotation of the magnet 13 to wind up the string 3. Specifically, supporting arms 32a and 32b are arranged to rotatably support two ends of the wind-up drum 31, and the axis of rotation of the magnet 13 is converted to an orthogonal axis of rotation via gears 33 to 35 such as bevel gears. In this case, if the wind-up drum 31 is made to sag in the middle, the wound-state of the string 3 can be made flat.

Further, in the first embodiment described above, a ratio of the rotation of the magnet 13 to the rotation of the rotor 12 or the wind-up drum 31 is not specifically mentioned; to obtain a predetermined ratio, a converter may be provided between the magnet 13 and the rotor 12, or between the magnet 13 and the wind-up drum 31 to convert the rotation ratio.

Second Embodiment

A second embodiment of the present invention will be described. In the first embodiment described above, the magnet 13 is made to rotate by the external rotating magnetic field, and the string 3 is wound up or brought out by the wind-up unit 10 which is linked to the rotation of the magnet 13. In the second embodiment, a driving unit that rotates the wind-up unit and a controller that drive controls the driving unit are provided, so that the string 3 is wound up or brought out by power in a capsule endoscope 2b.

Figure 5:
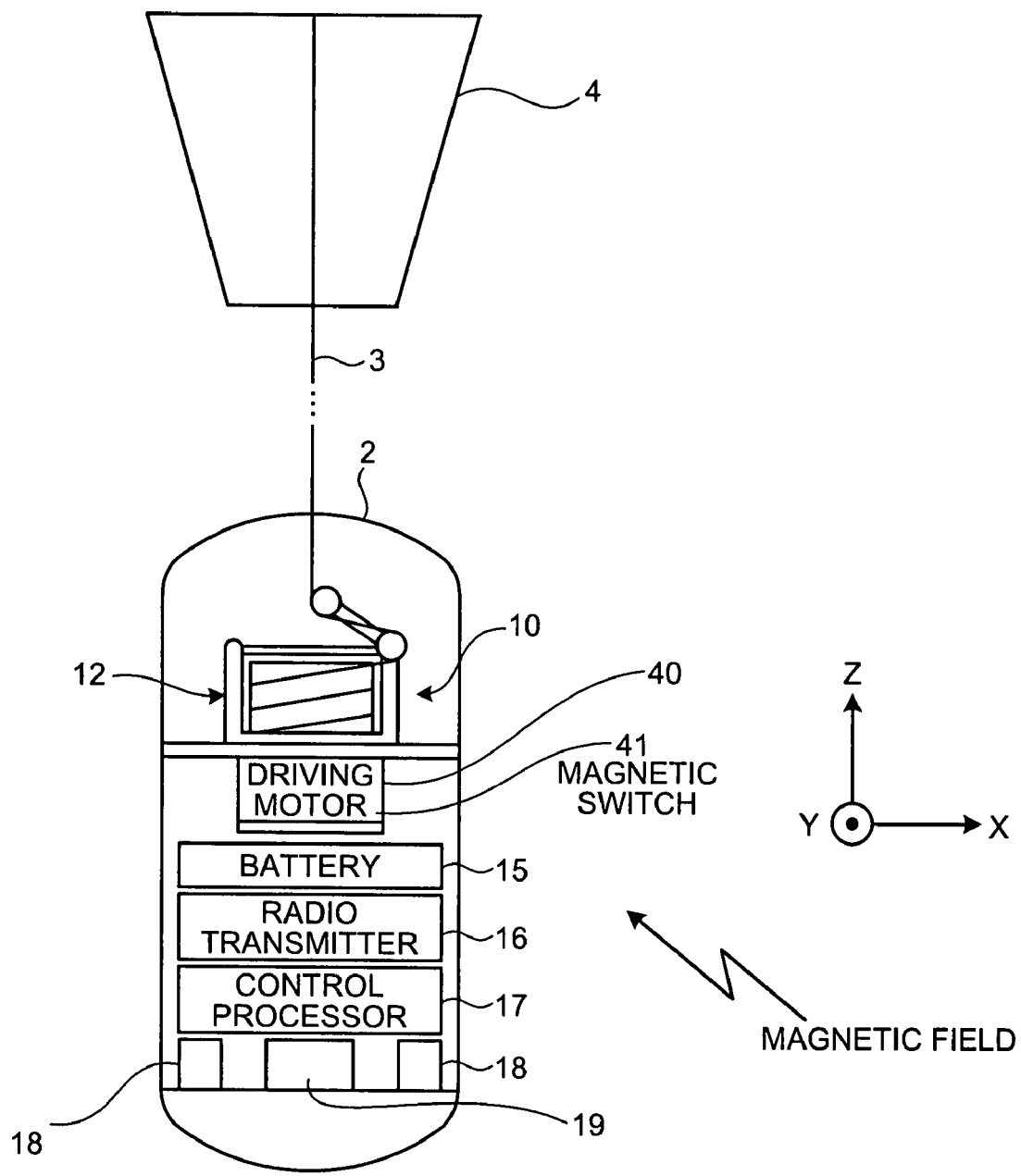
FIG. 5 is a sectional view showing a configuration of a capsule endoscope according to a-second embodiment of the present invention.

FIG. 5 is a sectional view showing a configuration of a capsule endoscope according to the second embodiment of the present invention. In FIG. 5, the capsule endoscope 2b includes a driving motor 40 that rotates the rotor 12 in place of the magnet 13, and a magnetic switch 41 that serves as a controller. Configuration of other elements is the same as the configuration of the first embodiment.

In the second embodiment, the magnetic-field generating unit 7 that generates the external rotating magnetic field is not necessary, and a magnetic-field generating unit that can merely generate a magnetic field in the subject 1 is sufficient. When the magnetic switch 41 detects a magnetic field generated by the magnetic-field generating unit, the driving motor 40 is made to rotate so as to cause the rotation of rotor 12 to wind up or bring out the string 3. It is preferable that the magnetic switch 41 include two magnetic switches that detect magnetic fields orthogonal to each other, and it is also preferable that the magnetic-field generating unit can generate magnetic fields orthogonal to each other. This is because, with such an arrangement, the direction of rotation of the driving motor 40 can be controlled based on the detection of the orthogonal magnetic fields.

Figure 6:
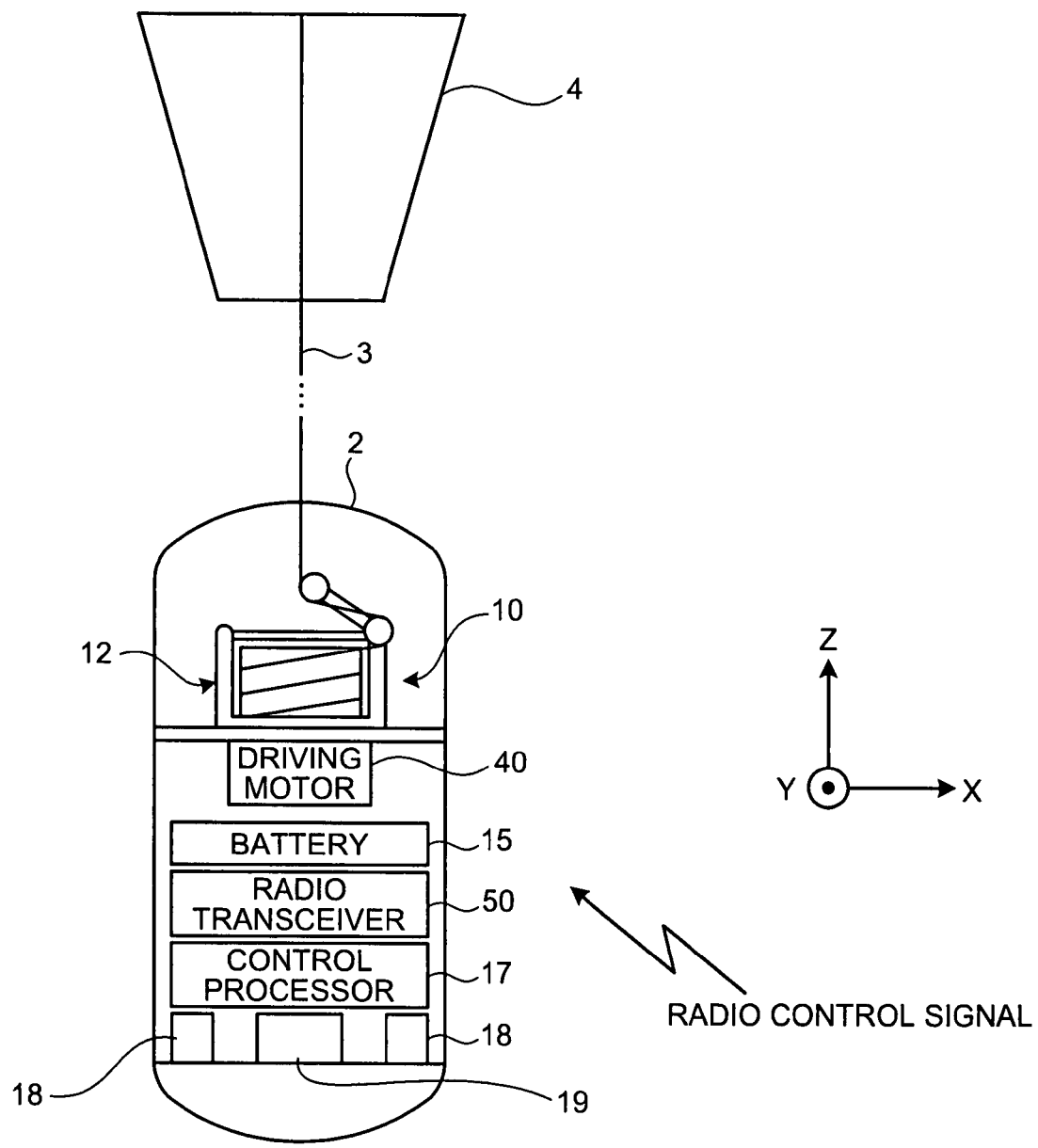
FIG. 6 is a sectional view showing a configuration of a capsule endoscope according to a modification of the second embodiment of the present invention.

It may be possible to provide a radio transceiver 50 that receives radio control signals as in a capsule endoscope 2c according to a modification of the second embodiment shown in FIG. 6 so as to control the rotation of the driving motor 40, instead of the magnetic switch 41 that detects the magnetic field. The capsule endoscope 2 according to the first embodiment and the capsule endoscope 2b shown in FIG. 5 both include the radio transmitter 16 that transmits information such as captured images and the like to the outside of the subject 1, though the radio transmitter 16 may be additionally provided with a radio receiver so as to form the radio transceiver 50, and the control processor 17 may control the rotation and the direction of the rotation of the driving motor 40 based on an control instruction indicated by a radio control signal received by the radio transceiver 50.

In the second embodiment, since the capsule endoscope 2b is provided with a driving source, the wind-up unit 10 can rotates securely and strongly.

Since the capsule endoscope and the intrasubject medical system using the same according to the present invention are provided with the wind-up unit that brings out and winds up the string in the main body of the capsule endoscope, the string itself does not move when the capsule endoscope moves, whereby the pharyngeal region is not hurt and desirable images can be obtained from throughout an interior of an organ even when the organ has a wide space as in the stomach.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As can be seen from the foregoing, the capsule endoscope and the intrasubject medical system using the same according to the present invention are useful for a capsule endoscope having a string whose one end is attached to a main body of the capsule endoscope and whose another end is arranged outside a subject and an intrasubject medical system using the same, and in particular, are suitable for a capsule endoscope whose main body can be moved by a wind-up unit arranged inside the main body of the capsule endoscope to wind up and bring out the string without hurting the pharyngeal region in the subject and in which desirable images can be acquired from throughout an interior of an organ even when the organ has a wide space, and an intrasubject medical system using the same.

What is claimed is:

1. A capsule endoscope comprising:
a string that has one end attached to a main body of the capsule endoscope and another end secured at a predetermined position;
a wind-up unit that is provided in the main body of the capsule endoscope to bring out and wind up the string; and
a magnet which is arranged in the main body of the capsule endoscope and which rotates according to an external rotating magnetic field generated outside a subject, wherein
the wind-up unit brings out and winds up the string in conjunction with rotation of the magnet.

2. The capsule endoscope according to claim 1, wherein the wind-up unit includes a rotor that rotates about a central axis of the main body of the capsule endoscope, and brings out and winds up the string according to rotation of the rotor.

3. The capsule endoscope according to claim 2, wherein the wind-up unit further includes a spool that is securely arranged in the main body of the capsule endoscope and winds up the string, and
the rotor rotates around the spool.

4. The capsule endoscope according to claim 1, wherein the wind-up unit includes a wind-up drum which rotates about an axis orthogonal to a central axis of the main body of the capsule endoscope and winds up the string.

5. The capsule endoscope according to claim 4, wherein the wind-up drum sags in the middle.

6. The capsule endoscope according to claim 1, further comprising
a driving unit that is arranged in the main body of the capsule endoscope and rotates the wind-up unit to bring out and wind up the string, and
a control unit that controls driving of the driving unit by receiving an external control signal.

7. The capsule endoscope according to claim 1, further comprising
a mouthpiece to which the another end of the string is secured.

8. An intrasubject medical system comprising:
a capsule endoscope having a string whose one end is attached to a main body of the capsule endoscope and whose another end is secured at a predetermined position, the capsule endoscope including inside the main body of the capsule endoscope an imaging unit, a radio transmitting unit that radio transmits an image captured by the imaging unit to an outside of a subject, a wind-up unit that brings out and winds up the string, and a magnet that is connected to the wind-up unit and rotates according to an external rotating magnetic field, the capsule endoscope brings out and winds up the string in conjunction with rotation of the magnet;
a receiving device that receives an image transmitted from the capsule endoscope; and
an external rotating magnetic field generating device that generates the external rotating magnetic field to rotate the magnet.

9. An intrasubject medical system comprising:
a capsule endoscope having a string whose one end is attached to a main body of the capsule endoscope and whose another end is secured at a predetermined position, the capsule endoscope including inside the main body of the capsule endoscope an imaging unit, a radio transmitting unit that radio transmits an image captured by the imaging unit to an outside of a subject, a wind-up unit that brings out and winds up the string, and a driving unit that is connected to the wind-up unit and rotates the wind-up unit to bring out and wind up the string, and a control unit that controls driving of the driving unit by receiving an external control signal including a magnetic field;
a receiving device that receives the image transmitted from the capsule endoscope; and
an external control signal generating device that transmits the external control signal to the control unit.

10. The intrasubject medical system according to claim 8 further comprising
a display unit that is connected to the receiving device to display the image transmitted from the capsule endoscope in real time, wherein
the external rotating magnetic field generating device is manipulated based on the image displayed on the display unit.

11. The intrasubject medical system according to claim 9, further comprising
a display unit that is connected to the receiving device to display the image transmitted from the capsule endoscope in real time, wherein
the external control signal generating device is manipulated based on the image displayed on the display unit.

* * * * *